United States Patent

Cunkle et al.

[11] Patent Number: 5,262,538
[45] Date of Patent: Nov. 16, 1993

[54] SUBSTITUTED 1-HYDROXY-2,6-DIARYL-4-ACYLOXYPIPERIDINES OR 1-HYDROXY-2,6-DIARYL-4-ACYLAMINOPIPERIDINES AND STABILIZED COMPOSITIONS

[75] Inventors: Glen T. Cunkle, Stamford, Conn.; Ramanathan Ravichandran, Nanuet; Donald J. Sabrsula, Peekskill, both of N.Y.

[73] Assignee: Ciba-Geigy Corporation, Ardsley, N.Y.

[21] Appl. No.: 945,076

[22] Filed: Sep. 15, 1992

Related U.S. Application Data

[62] Division of Ser. No. 696,695, May 7, 1991, Pat. No. 5,180,829.

[51] Int. Cl.$^5$ .............. C07D 401/12; C07D 211/46; C07D 211/58
[52] U.S. Cl. .................. 546/188; 546/190; 546/222; 546/224
[58] Field of Search .............. 546/216, 222, 224, 188, 546/190

[56] References Cited

U.S. PATENT DOCUMENTS

| | | | |
|---|---|---|---|
| 4,316,996 | 2/1982 | Collonge et al. | 568/784 |
| 4,668,721 | 5/1987 | Seltzer et al. | 524/95 |
| 4,782,105 | 1/1988 | Ravichandran et al. | 524/236 |
| 4,876,300 | 10/1989 | Seltzer et al. | 534/100 |
| 4,898,901 | 2/1990 | Ravichandran et al. | 524/237 |
| 5,015,683 | 5/1991 | Galbo | 546/186 |

FOREIGN PATENT DOCUMENTS 0309401  3/1989  European Pat. Off. .

OTHER PUBLICATIONS

Rajanavayanan et al "Deacetylation of N-acetyl-piperidin-4-ones by a novel electrochemical method" Tetrahedron Letters 32(31) 3873-3874 (1991).
H. Kothandraraman et al., J. Poly. Sci. Polymer Letters Ed., 23 475 (1985).
R. W. Murray et al., Syn. Comm. 23, 3509 (1989).
P. E. Eaton et al., J. Org. Chem., 1988, 53, 5353.
M. Balasubramanian et al., Tetrahedron 19, 2135 (1963).
P. Geneste, et al., J. Org. Chem., 41, 3437 (1976).
R. Haller et al., Tetrahedron 28, 2863 (1972).
M. Uma, et al., Indian J. Chem., 19B, 74 (1980).
Chem. Absts. 100, 120386k (1984).

*Primary Examiner*—C. Warren Ivy
*Assistant Examiner*—Celia Chang
*Attorney, Agent, or Firm*—Luther A. R. Hall

[57] ABSTRACT

Substituted 1-hydroxy-2,6-diaryl-4-acyloxypiperidines or 1-hydroxy-2,6-diaryl-4-acylaminopiperidines of formula I

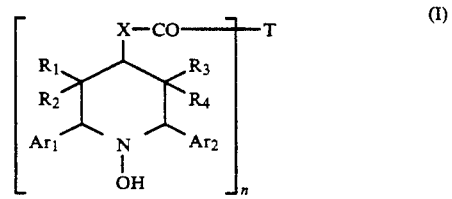

wherein n is 1-4, $Ar_1$ and $Ar_2$ are independently aryl or substituted aryl, $R_1$, $R_2$, $R_3$ and $R_4$ are independently hydrogen, alkyl, substituted alkyl, alkenyl, aryl or substituted aryl, X is —O— or —NE—, E is hydrogen, alkyl or cycloalkyl and T is an n-valent aliphatic or aromatic hydrocarbon radical, are effective in stabilizing organic materials against the deleterious effects of oxygen, heat and actinic radiation.

12 Claims, No Drawings

SUBSTITUTED 1-HYDROXY-2,6-DIARYL-4-ACYLOXYPIPERIDINES OR 1-HYDROXY-2,6-DIARYL-4-ACYLAMINOPIPERIDINES AND STABILIZED COMPOSITIONS

This is a divisional of application Ser. No. 07/696,695, filed on May 7, 1991, now U.S. Pat. No. 5,180,829, issued on Jan. 19, 1993.

The present invention pertains to novel substituted 1-hydroxy-2,6-diaryl-4-acyloxypiperidines or 1-hydroxy-2,6-diaryl-4-acylaminopiperidines and their use as stabilizers for various organic materials subject to the deleterious effects of oxygen, heat or actinic radiation. The instant compounds provide both melt flow stabilization and good color retention during processing as well as good retention of polymer physical properties during long-term thermooxidative stress.

BACKGROUND OF THE INVENTION

U.S. Pat. No. 4,316,996 teaches that 1-hydroxy-2,6-dialkylpiperidines are useful in preventing the discoloration of phenolic antioxidants.

1-Hydroxy-2,2,6,6-tetramethyl-4-acyloxypiperidines and other 1-hydroxy-2,2,6,6-tetramethylpiperidine derivatives are known as effective light stabilizers, but these compounds are not effective as processing stabilizers. They are also structurally distinct from the instant compounds of this invention.

U.S. Pat. Nos. 4,668,721; 4,782,105; 4,876,300 and 4,898,901 describe other hydroxylamines which are useful as processing stabilizers, but these hydroxylamines are structurally quite different from the instant compounds.

H. Kothandraraman et al., J. Poly. Sci. Polymer Letters Ed., 23, 475 (1985) report the preparation of polyacrylamides having the amino group substituted by selected substituted 2,6-diarylpiperidin-4-yl moieties. The instant compounds and their utility as stabilizers are not mentioned or suggested by this scientific article.

The instant 1-hydroxy-2,6-diaryl-4-acyloxypiperidines and 1-hydroxy-2,6-diaryl-4-acylaminopiperidines are novel compounds unknown in the prior art. The precursor amine starting materials are also novel compounds.

The 1-hydroxy-2,6-diaryl-4-acyloxypiperidines and 1-hydroxy-2,6-diaryl-4-acylaminopiperidines of this invention exhibit surprisingly superior properties compared to those of the closest prior art compounds.

The instant compounds are structurally distinct from prior art compounds. Their structures allow for the synthesis of high molecular weight compounds which have low volatility, better compatibility with the substrate and low extractability. The instant compounds provide both melt flow stabilization and good resistance against discoloration during polymer processing. The instant compounds have superior hydrolytic stability over the state of the art phosphite stabilizers and exhibit superior long term heat aging and oxidative induction time over the state of the art hydroxylamine stabilizers.

OBJECTS OF THE INVENTION

One object of this invention is to provide new substituted 1-hydroxy-2,6-diaryl-4-acyloxypiperidines or new 1-hydroxy-2,6-diaryl-4-acylaminopiperidines which are efficacious stabilizers for organic materials subject to oxidative, thermal and/or actinic degradation.

Another object of the invention is to provide stabilized compositions containing the substituted 1-hydroxy-2,6-diaryl-4-acyloxy-piperidines or 1-hydroxy-2,6-diaryl-4-acylaminopiperidines.

Still another object of this invention is to provide new substituted 2,6-diaryl-4-acyloxypiperidines or 2,6-diaryl-4-acylaminopiperidines which are useful as starting materials for making the 1-hydroxy-2,6-diaryl-4-acyloxypiperidine or 1-hydroxy-2,6-diaryl-4-acylaminopiperidine stabilizers of this invention.

DETAILED DISCLOSURE

The instant invention pertains to novel substituted 1-hydroxy-2,6-diaryl-4-acyloxypiperidines or 1-hydroxy-2,6-diaryl-4-acylaminopiperidines of formula I

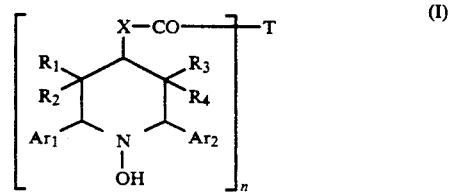

wherein
n is 1, 2, 3 or 4;
X is —O— or —NE—,
E is hydrogen, alkyl of 1 to 20 carbon atoms or cycloalkyl of 5 to 12 carbon atoms,
$Ar_1$ and $Ar_2$ are independently aryl of 6 to 10 carbon atoms; or said aryl substituted by one to three substituents selected from the group consisting of alkyl of 1 to 20 carbon atoms; cycloalkyl of 5 to 12 carbon atoms; phenylalkyl of 7 to 15 carbon atoms; —COOR$_5$ where R$_5$ is hydrogen or alkyl of 1 to 20 carbons; —COR$_6$ where R$_6$ is alkyl of 1 to 20 carbons; —NR$_7$R$_8$ where R$_7$ and R$_8$ are independently hydrogen or alkyl of 1 to 20 carbons; —SR$_9$ where R$_9$ is aryl of 6 to 10 carbon atoms or alkyl of 1 to 20 carbon atoms; —OH; —OCH$_3$; —CN; —CF$_3$; —NO$_2$; —F; —Cl; —Br and —I;
$R_1$, $R_2$, $R_3$ and $R_4$ are independently hydrogen; a linear or branched alkyl of 1 to 30 carbon atoms; or said alkyl terminated with —OR$_{10}$, —NR$_{11}$R$_{12}$, —SR$_{13}$, —COOR$_{14}$ or —CONR$_{15}$R$_{16}$, where R$_{10}$, R$_{11}$, R$_{12}$, R$_{13}$ and R$_{14}$ are independently alkyl of 1 to 20 carbon atoms or alkenyl of 3 to 18 carbon atoms, and R$_{15}$ and R$_{16}$ are independently hydrogen or the same meaning as R$_{10}$; or said alkyl interrupted by one or more —O—, —S—, —SO—, —SO$_2$—, —CO—, —COO—, —OCO—, —CONR$_{17}$—, —NR$_{17}$CO— or —NR$_{18}$— where R$_{17}$ and R$_{18}$ have the same meaning as R$_{15}$; alkenyl of 3 to 20 carbon atoms; aryl of 6 to 10 carbon atoms; or said aryl substituted by one to three substituents selected from the group consisting of alkyl of 1 to 20 carbon atoms, cycloalkyl of 5 to 12 carbon atoms, and phenylalkyl of 7 to 15 carbon atoms; and
when n is 1, T is alkyl of 1 to 20 carbon atoms or said alkyl interrupted by one or more of —O—, —S—, —SO—, —SO$_2$—, —CO—, —COO—, —OCO—, —CONR$_{19}$—, —NR$_{19}$CO— or —NR$_{20}$— where R$_{19}$ and R$_{20}$ have the same meaning as R$_{15}$; or aryl or substituted aryl having the same definition as $Ar_1$;
when n is 2, T is a direct bond; alkylene of 1 to 12 carbon atoms, or said alkylene interrupted by one or more of —O—, —S—, —SO—, —SO$_2$—, —CO—, —COO—, —OCO—, —CONR$_{21}$, —NR$_{21}$CO— or —NR$_{22}$— where R$_{21}$ and R$_{22}$ have the same meaning as R$_{15}$;

when n is 3, T is alkanetriyl of 3 to 8 carbon atoms; and when n is 4, T is alkanetetrayl of 4 to 10 carbon atoms.

All possible geometric isomers and stereoisomers which are predictable are to be included in the scope of this invention.

Preferably, n is 1 or 2.

Preferably X is —O—.

Preferably, Ar$_1$ and Ar$_2$ are the same and each is phenyl or phenyl substituted by methyl. Most preferably Ar$_1$ and Ar$_2$ are phenyl.

Preferably, R$_1$, R$_2$, R$_3$ and R$_4$ are independently hydrogen or methyl. Most preferably each of R$_1$, R$_2$, R$_3$ and R$_4$ is hydrogen; or R$_1$ is methyl, and R$_2$, R$_3$ and R$_4$ are hydrogen; or R$_1$ and R$_3$ are methyl, and R$_2$ and R$_4$ are hydrogen.

Preferably, when n is 1, T is alkyl of 1 to 17 carbon atoms; most preferably 7 to 17 carbon atoms.

Preferably, when n is 2, T is alkylene of 2 to 10 carbon atoms; most preferably 2 to 8 carbon atoms.

The instant invention also pertains to stabilized compositions containing (a) an organic material subject to oxidative, thermal or actinic degradation, and (b) an effective stabilizing amount of a compound of formula I as defined above.

The oxidation of secondary amines to hydroxylamines using dimethyloxirane has been reported by Murray and Singh, Synthetic Comm. 1989, 19, 3509. The instant compounds are prepared by the oxidation of the corresponding amine with dimethyldioxirane by the procedure of Eaton and Wicks, J. Org. Chem. 1988, 53, 5353. The corresponding amine is conveniently prepared by the acylation of the corresponding 4-hydroxypiperidine or 4-aminopiperidine.

These substituted 4-hydroxypiperidines, such as 2,6-diphenyl-4-hydroxypiperidine, 2,6-diphenyl-3-methyl-4-hydroxypiperidine and 2,6-diphenyl-3,5-dimethyl-4-hydroxypiperidine, are prepared by published procedures, Balasubramanian, M.; Padma, N., Tetrahedron 19, 2135 (1963).

The 2,6-diaryl-4-aminopiperidines are synthesized by oximation of the corresponding ketone as taught by P. Geneste et al., J. Org. Chem. 41, 3437 (1976) and R. Haller et al., Tetrahedron, 28, 2863 (1972); followed by reduction to the primary amine as taught by M. Uma et al., Indian J. Chem., 19B, 74 (1980).

Another aspect of the instant invention is the amine starting materials of formula II

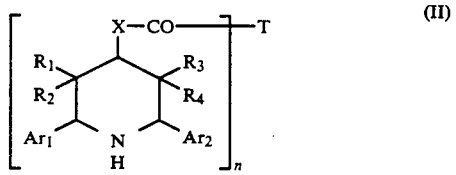

(II)

used to prepare the instant compounds of formula I. These have the same definitions as cited above for formula I except that there is no hydroxyl group on the N atom in the piperidine ring in the amine precursor starting material.

When any of Ar$_1$, Ar$_2$, R$_1$ to R$_{23}$, E or T is alkyl, such alkyl groups are, for example, methyl, ethyl, isopropyl, n-butyl, tert-butyl, tert-amyl, 2-ethylhexyl, n-octyl, n-undecyl, lauryl, n-heptadecyl, n-octadecyl and eicosyl; when said radicals are cycloalkyl, they are, for example, cyclopentyl, cyclohexyl, cyclooctyl and cyclododecyl; when said radicals are phenylalkyl, they are, for example, benzyl, phenethyl, α-methylbenzyl and α,α-dimethylbenzyl; when said radicals are aryl, they are, for example phenyl, naphthyl, or when substituted by alkyl are, for example, tolyl and xylyl; when said radicals are alkyl interrupted by -O-, they are for example, 3-oxaamyl and 3,6-dioxaoctyl; when T is alkyl or said alkyl interrupted by -O-, T is, for example, methylene, ethylene, trimethylene, tetramethylene, octamethylene, 2,2-dimethylpropane-1,3-diyl, 3-oxapentamethylene and 3,6-dioxaoctamethylene; when T is alkanetriyl, it is, for example, glyceryl, trimethylyl propane; and when T is alkanetetrayl, T is, for example, pentaerythrityl or 1,2,3,4-butanetetrayl.

Substrates in which the instant compounds of formula I are particularly useful are polyolefins, such as polyethylene and polypropylene. Polypropylene is particularly well stabilized by the instant compounds during processing.

While the instant compounds of formula I are quite effective process stabilizers for polyolefins when used alone, compositions which also contain a phenolic antioxidant are also extremely well stabilized during processing by this combination of process stabilizers.

In general polymers which can be stabilized include

1. Polymers of monoolefins and diolefins, for example polyethylene (which optionally can be crosslinked), polypropylene, polyisobutylene, polybutene-1, polymethylpentene-1, polyisoprene or polybutadiene, as well as polymers of cycloolefins, for instance of cyclopentene or norbornene.

2. Mixtures of the polymers mentioned under 1), for example mixtures of polypropylene with polyisobutylene.

3. Copolymers of monoolefins and diolefins with each other or with other vinyl monomers, such as, for example, ethylene/propylene, propylene/butene-1, propylene/isobutylene, ethylene/butene-1, propylene/butadiene, isobutylene/isoprene, ethylene/alkyl acrylates, ethylene/alkyl methacrylates, ethylene/vinyl acetate or ethylene/acrylic acid copolymers and their salts (ionomers) and terpolymers of ethylene with propylene and a diene, such as hexadiene, dicyclopentadiene or ethylidene-norbornene.

4. Polystyrene, poly-(p-methylstyrene).

5. Copolymers of styrene or methylstyrene with dienes or acrylic derivatives, such as, for example, styrene/butadiene, styrene/acrylonitrile, styrene/ethyl methacrylate, styrene/butadiene/ethyl acrylate, styrene/acrylonitrile/methyl acrylate; mixtures of high impact strength from styrene copolymers and another polymer, such as, for example, from a polyacrylate, a diene polymer or an ethylene/propylene/diene terpolymer; and block polymers of styrene, such as, for example, styrene/butadiene/styrene, styrene/isoprene/styrene, styrene/ethylene/butylene/styrene or styrene/ethylene/propylene/styrene.

6. Graft copolymers of styrene, such as, for example, styrene on polybutadiene, styrene and acrylonitrile on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures thereof with the copolymers listed under 5), for instance the copolymer mixtures known as ABS-, MBS-, ASA- or AES-polymers.

7. Halogen-containing polymers, such as polychloroprene, chlorinated rubbers, chlorinated or sulfochlorinated polyethylene, epichlorohydrin homo- and copolymers, polymers from halogen-containing vinyl compounds, as for example, polyvinylchloride, polyvinylidene chloride, polyvinyl fluoride, polyvinylidene fluoride, as well as copolymers thereof, as for example, vinyl chloride/vinylidene chloride, vinyl chloride/vinyl acetate, vinylidene chloride/vinyl acetate copolymers, or vinyl fluoride/vinyl ether copolymers.

8. Polymers which are derived from $\alpha,\beta$-unsaturated acids and derivatives thereof, such as polyacrylates and polymethacrylates, polyacrylamide and polyacrylonitrile.

9. Copolymers from the monomers mentioned under 8) with each other or with other unsaturated monomers, such as, for instance, acrylonitrile/butadiene, acrylonitrile/alkyl acrylate, acrylonitrile/alkoxyalkyl acrylate or acrylonitrile/vinyl halogenide copolymers or acrylonitrile/alkyl methacrylate/butadiene terpolymers.

10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinylbutyral, polyallyl phthalate or polyallyl-melamine.

11. Homopolymers and copolymers of cyclic ethers, such as polyalkylene glycols, polyethylene oxide, polypropylene oxide or copolymers thereof with bis-glycidyl ethers.

12. Polyacetals, such as polyoxymethylene and those polyoxymethylenes which contain ethylene oxide as comonomer.

13. Polyphenylene oxides and sulfides, and mixtures of polyphenylene oxides with polystyrene.

14. Polyurethanes which are derived from polyethers, polyesters or polybutadienes with terminal hydroxyl groups on the one side and aliphatic or aromatic polyisocyanates on the other side, as well as precursors thereof (polyisocyanates, polyols or prepolymers).

15. Polyamides and copolyamides which are derived from diamines and dicarboxylic acids and/or from aminocarboxylic acids or the corresponding lactams, such as polyamide 4, polyamide 6, polyamide 6/6, polyamide 6/10, polyamide 11, polyamide 12, poly-2,4,4-trimethylhexamethylene terephthalamide, poly-p-phenylene terephthalamide or poly-m-phenylene isophthalamide, as well as copolymers thereof with polyethers, such as for instance with polyethylene glycol, polypropylene glycol or polytetramethylene glycols.

16. Polyureas, polyimides and polyamide-imides.

17. Polyesters which are derived from dicarboxylic acids and diols and/or from hydroxycarboxylic acids or the corresponding lactones, such as polyethylene terephthalate, polybutylene terephthalate, poly- 1,4-dimethylol-cyclohexane terephthalate, poly-[2,2-(4-hydroxyphenyl)-propane] terephthalate and polyhydroxybenzoates as well as block-copolyether-esters derived from polyethers having hydroxyl end groups.

18. Polycarbonates.

19. Polysulfones, polyethersulfones and polyetherketones.

20. Crosslinked polymers which are derived from aldehydes on the one hand and phenols, ureas and melamines on the other hand, such as phenol/formaldehyde resins, urea/formaldehyde resins and melamine/formaldehyde resins.

21. Drying and non-drying alkyd resins.

22. Unsaturated polyester resins which are derived from copolyesters of saturated and unsaturated dicarboxylic acids with polyhydric alcohols and vinyl compounds as crosslinking agents, and also halogen-containing modifications thereof of low flammability.

23. Thermosetting acrylic resins, derived from substituted acrylic esters, such as epoxy-acrylates, urethaneacrylates or polyester acrylates.

24. Alkyd resins, polyester resins or acrylate resins in admixture with melamine resins, urea resins, polyisocyanates or epoxide resins as crosslinking agents.

25. Crosslinked epoxide resins which are derived from polyepoxides, for example from bis-glycidyl ethers or from cycloaliphatic diepoxides.

26. Natural polymers, such as cellulose, rubber, gelatin and derivatives thereof which are chemically modified in a polymer homologous manner, such as cellulose acetates, cellulose propionates and cellulose butyrates, or the cellulose ethers, such as methyl cellulose.

27. Mixtures of polymers as mentioned above, for example PP/EPDM, Polyamide 6/EPDM or ABS, PVC/EVA, PVC/ABS, PVC/MBS, PC/ABS, PBTP/ABS.

28. Naturally occuring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, which materials may be used as plasticizers for polymers or as textile spinning oils, as well as aqueous emulsions of such materials.

29. Aqueous emulsions of natural or synthetic rubber, e.g. natural latex or latices of carboxylated styrene/butadiene copolymers.

30. Polysiloxanes such as the soft, hydrophilic polysiloxanes described, for example, in U.S. Pat. No. 4,259,467; and the hard polyorganosiloxanes described, for example, in U.S. Pat. No. 4,355,147.

31. Polyketimines in combination with unsaturated acrylic polyacetoacetate resins or with unsaturated acrylic resins. The unsaturated acrylic resins include the urethane acrylates, polyether acrylates, vinyl or acryl copolymers with pendant unsaturated groups and the acrylated melamines. The polyketimines are prepared from polyamines and ketones in the presence of an acid catalyst.

32. Radiation curable compositions containing ethylenically unsaturated monomers or oligomers and a polyunsaturated aliphatic oligomer.

33. Epoxymelamine resins such as light-stable epoxy resins crosslinked by an epoxy functional coetherified high solids melamine resin such as LSE-4103 (Monsanto).

In general, the compounds of the present invention are employed in from about 0.01 to about 5% by weight of the stabilized composition, although this will vary with the particular substrate and application. An advantageous range is from about 0.5 to about 2%, and especially 0.1 to about 1%.

The stabilizers of the instant invention may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The resulting stabilized polymer compositions of the invention may optionally also contain from about 0.01 to about 5%, preferably from about 0.025 to about 2%, and especially from about 0.1 to about 1% by weight of various conventional additives, such as the materials listed below, or mixtures thereof.

1. Antioxidants 1.1 Alkylated monophenols, for example,
2,6-di-tert-butyl-4-methylphenol
2-tert.butyl-4,6-dimethylphenol
2,6-di-tert-butyl-4-ethylphenol
2,6-di-tert-butyl-4-n-butylphenol
2,6-di-tert-butyl-4-i-butylphenol
2,6-di-cyclopentyl-4-methylphenol
2-(α-methylcyclohexyl)-4,6-dimethylphenol
2,6-di-octadecyl-4-methylphenol
2,4,6-tri-cyclohexylphenol
2,6-di-tert-butyl-4-methoxymethylphenol 1.2. Alkylated hydroquinones, for example,
2,6-di-tert-butyl-4-methoxyphenol
2,5-di-tert-butyl-hydroquinone
2,5-di-tert-amyl-hydroquinone
2,6-diphenyl-4-octadecyloxyphenol 1.3. Hydroxylated thiodiphenyl ethers, for example,
2,2'-thio-bis-(6-tert-butyl-4-methylphenol)
2,2'-thio-bis-(4-octylphenol)
4,4'-thio-bis-(6-tert-butyl-3-methylphenol)
4,4'-thio-bis-(6-tert-butyl-2-methylphenol)

1.4. Alkylidene-bisphenols, for example,
2,2'-methylene-bis-(6-tert-butyl-4-methylphenol)
2,2'-methylene-bis-(6-tert-butyl-4-ethylphenol)
2,2'-methylene-bis-[4-methyl-6-(α-methylcyclohexyl)-phenol]
2,2'-methylene-bis-(4-methyl-6-cyclohexylphenol)
2,2'-methylene-bis-(6-nonyl-4-methylphenol)
2,2'-methylene-bis-[6-(α-methylbenzyl)-4-nonylphenol]
2,2'-methylene-bis-[6-(α,α-dimethylbenzyl)-4-nonylphenol]
2,2'-methylene-bis-(4,6-di-tert-butylphenol)
2,2'-ethylidene-bis-(4,6-di-tert-butylphenol)
2,2'-ethylidene-bis-(6-tert-butyl-4-isobutylphenol)
4,4'-methylene-bis-(2,6-di-tert-butylphenol)
4,4'-methylene-bis-(6-tert-butyl-2-methylphenol)
1,1-bis-(5-tert-butyl-4-hydroxy-2-methylphenyl-butane
2,6-di-(3-tert-butyl-5-methyl-2-hydroxybenzyl)-4-methylphenol
1,1,3-tris-(5-tert-butyl-4-hydroxy-2-methylphenyl)-butane
1,1-bis-(5-tert-butyl-4-hydroxy-2-methylphenyl)-3-n-dodecylmercaptobutane
ethyleneglycol  .bis-[3,3-bis-(3'-tert-butyl-4'-hydroxyphenyl)-butyrate]
di-(3-tert-butyl-4-hydroxy-5-methylphenyl)-dicyclopentadiene
di-[2-(3'-tert-butyl-2'-hydroxy-5'-methyl-benzyl)-6-tert-butyl-4-methylphenyl] terephthalate.

1.5. Benzyl compounds, for example,
1,3,5-tri-(3,5-di-tert-butyl-4-hydroxybenzyl)-2,4,6-trimethylbenzene
di-(3,5-di-tert-butyl-4-hydroxybenzyl) sulfide
3,5-di-tert-butyl-4-hydroxybenzyl-mercapto-acetic acid isooctyl ester
bis-(4-tert-butyl-3-hydroxy-2,6-dimethylbenzyl)dithiol terephthalate 1,3,5-tris-(3,5-di-tert-butyl-4-hydroxybenzyl) isocyanurate
1,3,5-tris-(4-tert-butyl-3-hydroxy-2,6-dimethylbenzyl) isocyanurate
3,5-di-tert-butyl-4-hydroxybenzyl-phosphoric acid dioctadecyl ester
3,5-di-tert-butyl-4-hydroxybenzyl-phosphoric acid monoethyl ester, calcium-salt 1.6. Acylaminophenols, for example,
4-hydroxy-lauric acid anilide
4-hydroxy-stearic acid anilide
2,4-bis-octylmercapto-6-(3,5-tert-butyl-4-hydroxyanilino)-s-triazine
octyl-N-(3,5-di-tert-butyl-4-hydroxyphenyl)-carbamate 1.7. Esters of β-(3,5-di-tert-butyl-4-hydroxyphenyl)-propionic acid with monohydric or polyhydric alcohols, for example,

| methanol | diethylene glycol |
|---|---|
| octadecanol | triethylene glycol |
| 1,6-hexanediol | pentaerythritol |
| neopentyl glycol | tris-hydroxyethyl isocyanurate |
| thiodiethylene glycol | di-hydroxyethyl oxalic acid diamide |

1.8. Esters of β-(5-tert-butyl-4-hydroxy-3-methylphenyl)-propionic acid with monohydric or polyhydric alcohols, for example,

| methanol | diethylene glycol |
|---|---|
| octadecanol | triethylene glycol |
| 1,6-hexanediol | pentaerythritol |
| neopentyl glycol | tris-hydroxyethyl isocyanurate |
| thiodiethylene glycol | di-hydroxyethyl oxalic acid diamide |

1.9. Amides of β-(3,5-di-tert-butyl-4-hydroxyphenyl)-propionic acid for example,
N,N'-di-(3,5-di-tert-butyl-4-hydroxyphenylpropionyl)-hexamethylenediamine
N,N'-di-(3,5-di-tert-butyl-4-hydroxyphenylpropionyl)-trimethylenediamine
N,N'-di-(3,5-di-tert-butyl-4-hydroxyphenylpropionyl)-hydrazine 1.10 Diarylamines, for example,
diphenylamine, N-phenyl-1-naphthylamine, N-(4-tert-octylphenyl)-1-naphthylamine,
4,4'-di-tert-octyl-diphenylamine, reaction product of N-phenylbenzylamine and 2,4,4-trimethylpentene, reaction product of diphenylamine and 2,4,4-trimethylpentene, reaction product of N-phenyl-1-naphthylamine and 2,4,4-trimethylpentene.

2. UV absorbers and light stabilizers 2.1. 2-(2'-Hydroxyphenyl)-benzotriazoles, for example, the 5'-methyl-, 3',5'-di-tert-butyl-, 5'-tert-butyl-, 5'-(1,1,3,3-tetramethylbutyl)-, 5-chloro-3',5'-di-tert-butyl-, 5-chloro-3'-tert-butyl-5'-methyl-, 3'-sec-butyl-5'-tert-butyl-, 4'-octoxy, 3',5'-di-tert-amyl-, 3',5'-bis-(α,α-dimethylbenzyl), 3'-tert-butyl-5'-(2-(omega-hydroxy-octa-(ethyleneoxy)carbonyl-ethyl)-, 3'-dodecyl-5'-methyl, and 3'-tert-butyl-5'-(2-octyloxycarbonyl)ethyl-, and dodecylated-5'-methyl derivatives.

2.2. 2-Hydroxy-benzophenones, for example, the 4-hydroxy-, 4-methoxy-, 4-octoxy, 4-decyloxy-, 4-dodecyloxy-, 4-benzyloxy, 4,2',4'-trihydroxy- and 2'-hydroxy-4,4'-dimethoxy derivatives.

2.3. Esters of optionally substituted benzoic acids for example, phenyl salicylate, 4-tert-butylphenyl salicylate, octylphenyl salicylate, dibenzoylresorcinol, bis-(4-tert-butylbenzoyl)-resorcinol, benzoylresorcinol, 3,5-di-tert-butyl-4-hydroxybenzoic acid 2,4-di-tert-butylphenyl ester and 3,5-di-tert-butyl-4-hydroxybenzoic acid hexadecyl ester.

2.4. Acrylates, for example, α-cyano-β,β-diphenylacrylic acid ethyl ester or isooctyl ester, α-carbomethoxy-cinnamic acid methyl ester, α-cyano-β-methyl-p-methoxy-cinnamic acid methyl ester or butyl ester, α-carbomethoxy-p-methoxy-cinnamic acid methyl ester, N-(β-carbomethoxy-β-cyanovinyl)-2-methyl-indoline.

2.5. Nickel compounds, for example, nickel complexes of 2,2'-thio-bis-[4-(1,1,3,3-tetramethylbutyl)-phenol], such as the 1:1 or 1:2 complex, optionally with additional ligands such as n-butylamine, triethanolamine or N-cyclohexyl-diethanolamine, nickel dibutyldithiocarbamate, nickel salts of 4-hydroxy-3,5-di-tert-butylbenzylphosphonic acid monoalkyl esters, such as of the methyl, ethyl or butyl ester, nickel complexes of ketoximes such as of 2-hydroxy-4-methyl-phenyl undecyl ketoxime, nickel complexes of 1-phenyl-4-lauroyl-5-hydroxy-pyrazole, optionally with additional ligands.

2.6. Sterically hindered amines, for example, bis-(2,2,6,6-tetramethylpiperidyl) sebacate, bis-(1,2,2,6,6-pentamethylpiperidyl) sebacate, n-butyl-3,5-di-tert.butyl-4-hydroxybenzyl malonic acid bis-(1,2,2,6,6-pentanemethylpiperidyl)ester, condensation product of 1-hydroxyethyl-2,2,6,6-tetramethyl-4-hydroxypiperidine and succinic acid, condensation product of N,N'-(2,2,6,6-tetramethylpiperidyl)-hexamethylenediamine and 4-tert-octylamino-2,6-dichloro-s-triazine, tris-(2,2,6,6-tetramethylpiperidyl)-nitrilotriacetate, tetrakis-(2,2,6,6-tetramethyl-4-piperidyl) 1,2,3,4-butanetetracarboxylate, 1,1'(1,2-ethanediyl)-bis-(3,3,5,5-tetramethylpiperazinone).

2.7. Oxalic acid diamides, for example, 4,4'-dioctyloxy-oxanilide, 2,2'-di-octyloxy-5,5'-di-tert-butyl-oxanilide, 2,2'-di-dodecyloxy-5,5'-di-tert-butyl-oxanilide, 2-ethoxy-2'-ethyl-oxanilide, N,N'-bis (3-dimethylaminopropyl)-oxalamide, 2-ethoxy-5-tert-butyl-2'-ethyloxanilide and its mixture with 2-ethoxy-2'-ethyl-5,4'-di-tert-butyloxanilide and mixtures of ortho- and para-methoxy- as well as of o- and p-ethoxy-disubstituted oxanilides.

2.8. Hydroxyphenyl-s-triazines, for example 2,6-bis-(2,4-dimethylphenyl)-4-(2-hydroxy-4-octyloxyphenyl)-s-triazine; 2,6-bis-(2,4-dimethylphenyl)-4-(2,4-dihydroxyphenyl)-s-triazine; 2,4-bis(2,4-dihydroxyphenyl)-6-(4-chlorophenyl)-s-triazine; 2,4-bis[2-hydroxy-4-(2-hydroxyethoxy)phenyl]-6-(4-chlorophenyl)-s-triazine; 2,4-bis[2-hydroxy-4-(2-hydroxy-4-(2-hydroxyethoxy)-phenyl]-6-(2,4-dimethylphenyl)-s-triazine; 2,4-bis[2-hydroxy-4-(2-hydroxyethoxy)phenyl]-6-(4-bromophenyl)-s-triazine; 2,4-bis[2-hydroxy-4-(2-acetoxyethoxy)phenyl]-6-(4-chlorophenyl)-s-triazine, 2,4-bis(2,4-dihydroxyphenyl)-6-(2,4-dimethylphenyl)-s-triazine.

3. Metal deactivators, for example, N,N'-diphenyloxalic acid diamide, N-salicylal-N'-salicyloylhydrazine, N,N'-bis-salicyloylhydrazine, N,N'-bis-(3,5-di-tert-butyl-4-hydroxyphenylpropionyl)hydrazine, 3-salicyloylamino-1,2,4-triazole, bis-benzylidene-oxalic acid dihydrazide.

4. Phosphites and phosphonites, for example, triphenyl phosphite, diphenylalkyl phosphites, phenyldialkyl phosphites, tri-(nonylphenyl) phosphite, trilauryl phosphite, trioctadecyl phosphite, di-stearyl-pentaerythritol diphosphite, tris-(2,4-di-tert-butylphenyl) phosphite, di-isodecylpentaerythritol diphosphite, di-(2,4-di-tert-butylphenyl)pentaerythritol diphosphite, tristearylsorbitol triphosphite, tetrakis-(2,4-di-tert-butylphenyl) 4,4'-diphenylylenediphosphonite.

5. Compounds which destroy peroxide, for example, esters of β-thiodipropionic acid, for example the lauryl, stearyl, myristyl or tridecyl esters, mercapto-benzimidazole or the zinc salt of 2-mercaptobenzimidazole, zinc dibutyl-dithiocarbamate, dioctadecyl disulfide, pentaerythritol tetrakis-(β-dodecylmercapto)-propionate.

6. Hydroxylamines, for example, N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

7. Nitrones, for example, N-benzyl-alpha-phenyl nitrone, N-ethyl-alpha-methyl nitrone, N-octyl-alpha-heptyl nitrone, N-lauryl-alpha-undecyl nitrone, N-tetradecyl-alpha-tridecyl nitrone, N-hexadecyl-alpha-pentadecyl nitrone, N-octadecyl-alpha-heptadecylnitrone, N-hexadecyl-alpha-heptadecyl nitrone, N-octadecyl-alpha-pentadecyl nitrone, N-heptadecyl-alpha-heptadecyl nitrone, N-octadecyl-alpha-hexadecyl nitrone, derived from N,N-dialkylhydroxylamine derived from hydrogenated tallow amine.

8. Polyamide stabilizers, for example copper salts in combination with iodides and/or phosphorus compounds and salts of divalent manganese.

9. Basic co-stabilizers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example Ca stearate, Zn stearate, Mg stearate, Na ricinoleate and K palmitate, antimony pyrocatecholate or zinc pyrocatecholate.

10. Nucleating agents, for example, 4-tert-butyl-benzoic acid, adipic acid, diphenylacetic acid.

11. Fillers and reinforcing agents, for example, calcium carbonate, silicates, glass fibers, asbestos, talc, kaolin, mica, barium sulfate, metal oxides and hydroxides, carbon black, graphite.

12. Other additives, for example, plasticizers, lubricants, emulsifiers, pigments, optical brighteners, flameproofing agents, anti-static agents, blowing agents and thiosynergists such as dilauryl thiodipropionate or distearyl thiodipropionate.

The phenolic antioxidant of particular interest is selected from the group consisting of n-octadecyl 3,5-di-tert-butyl-4-hydroxyhydrocinnamate, neopentanetetrayl tetrakis(3,5-di-tert-butyl-4-hydroxyhydrocinnamate), di-n-octadecyl 3,5-di-tert-butyl-4-hydroxybenzylphosphonate, 1,3,5-tris(3,5-di-tert-butyl-4-hydroxybenzyl)isocyanurate, thiodiethylene bis(3,5-di-tert-butyl-4-hydroxyhydrocinnamate), 1,3,5-trimethyl-2,4,6-tris(3,5-di-tert-butyl-4-hydroxybenzyl)-benzene, 3,6-dioxaoctamethylene bis(3-methyl-5-tert-butyl-4-hydroxyhydrocinnamate), 2,6-di-tert-butyl-p-cresol, 2,2'-ethylidene-bis(4,6-di-tert-butylphenol), 1,3,5-tris(2,6-dimethyl-4-tert-butyl-3-hydroxybenzyl)isocynurate, 1,1,3-tris(2-methyl-4-hydroxy-5-tert-butylphenyl)butane, 1,3,5-tris[2-(3,5-di-tert-butyl-4-hydroxyhydrocinnamoyloxy)ethyl]isocyanurate, 3,5-di-(3,5-di-tert-butyl-4-hydroxybenzyl)mesitol, hexamethylene bis(3,5-di-tert-butyl-4-hydroxyhydrocinnamate), 1-(3,5-di-tert-butyl-4-hydroxyanilino)-3,5-di(octylthio)-s-triazine, N,N'-hexamethylene-bis(3,5-di-tert-butyl-4-hydroxyhydrocinnamamide), calcium bis(ethyl 3,5-di-tert-butyl-4-hydroxybenzylphosphonate), ethylene bis[3,3-di(3-tert-butyl-4-hydroxyphenyl)butyrate], octyl 3,5-di-tert-butyl-4-hydroxybenzylmercaptoacetate, bis(3,5-di-tert-butyl-4-hydroxyhydrocinnamoyl)hydrazide, and N,N'-bis[2-(3,5-di-tert-butyl-4-hydroxyhydrocinnamoyloxy)-ethyl]-oxamide.

A most preferred phenolic antioxidant is neopentanetetrayl tetrakis(3,5-di-tert-butyl-4-hydroxyhydrocinnamate), n-octadecyl 3,5-di-tert-butyl-4-hydroxyhydrocinnamate, 1,3,5-trimethyl-2,4,6-tris(3,5-di-tert-butyl-4-hydroxybenzyl)benzene, 1,3,5-tris(3,5-di-tert-butyl-4-hydroxybenzyl)isocyanurate, 2,6-di-tert-butyl-p-cresol or 2,2'-ethylidene-bis(4,6-di-tert-butylphenol).

The hindered amine compound of particular interest is selected from the group consisting of
bis(2,2,6,6-tetramethylpiperidin-4-yl) sebacate,
bis(1,2,2,6,6-pentamethylpiperidin-4-yl) sebacate,
di(1,2,2,6,6-pentamethylpiperidin-4-yl) (3,5-di-tert-butyl-4-hydroxybenzyl)butylmalonate,
4-benzoyl-2,2,6,6-tetramethylpiperidine, 4-stearyloxy-2,2,6,6-tetramethylpiperidine,
3-n-octyl-7,7,9,9-tetramethyl-1,3,8-triaza-spiro[4.5]decane-2,4-dione,
tris(2,2,6,6-tetramethylpiperidin-4-yl) nitrilotriacetate,
1,2-bis(2,2,6,6-tetramethyl-3-oxopiperazin-4-yl)ethane,
2,2,4,4-tetramethyl-7-oxa-3,20-diaza-21-oxodispiro[5.1.11.2] heneicosane, polycondensation product of 2,4-dichloro-6-tert-octylamino-s-triazine and 4,4'-hexamethylenebis(amino-2,2,6,6-tetramethylpiperidine), polycondensation product of 1-(2-hydroxyethyl)-2,2,6,6-tetramethyl-4-hydroxypiperidine and succinic acid, polycondensation product of 4,4'-hexamethylenebis-(amino-2,2,6,6-tetramethylpiperidine) and 1,2-dibromoethane, tetrakis(2,2,6,6-tetramethylpiperidin-4-yl) 1,2,3,4-butanetetracarboxylate, tetrakis(1,2,2,6,6-pentamethylpiperidin-4-yl) 1,2,3,4-butanetetracarboxylate, polycondensation product of 2,4-dichloro-6-morpholino-s-triazine and 4,4'-hexamethylenebis(amino-2,2,6,6-tetramethylpiperidine), N,N',N'',N'''-tetrakis[(4,6-bis(butyl-2,2,6,6-tetramethyl-piperidin-4-yl)-amino-s-triazin-2-yl]-1,10-diamino-4,7-diazadecane, mixed [2,2,6,6-tetramethylpiperidin-4-yl/$\beta,\beta,\beta',\beta'$-tetramethyl-3,9-(2,4,8,10-tetraoxaspiro[5.5]-undecane) diethyl] 1,2,3,4-butanetetracarboxylate, mixed [1,2,2,6,6-pentamethylpiperidin-4-yl/$\beta,\beta,\beta',\beta'$-tetramethyl-3,9-(2,4,8,10-tetraoxaspiro[5.5]-undecane)diethyl] 1,2,3,4-butanetetracarboxylate, octamethylene bis(2,2,6,6-tetramethylpiperidin-4-carboxylate) and
4,4'-ethylenebis(2,2,6,6-tetramethylpiperazin-3-one).

A most preferred hindered amine compound is bis(2,2,6,6-tetramethylpiperidin-4-yl) sebacate, the polycondensation product of 1-(2-hydroxyethyl)-2,2,6,6-tetramethyl-4-hydroxypiperdine and succinic acid, the polycondensation product of 2,4-dichloro-6-tert-octylaminos-triazine and 4,4'-hexamethylenebis-(amino-2,2,6,6-tetramethylpiperidine) or N,N',N'',N'''-tetrakis[(4,6-bis(butyl-(2,2,6,6-tetramethyl-piperidin-4-yl)amino)-s-triazine-2-yl]-1,10-diamino-4,7-diazadecane.

The following examples are presented for the purpose of illustration only and are not to be construed to limit the nature or scope of the instant invention in any manner whatsoever.

EXAMPLE 1

2,6-Diphenylpiperidin-4-yl Laurate

To a −70° C. solution of 2.50 g (9.9 mmol) of 2,6-diphenyl-4-hydroxypiperidine in 80 ml of dry tetrahydrofuran (THF), 4.2 mL (10.5 mmol) of n-butyllithium (2.5M in hexanes) is added dropwise. The mixture is warmed to −20° C. and stirred for 30 minutes. The solution is then cooled again to −70° C. and a solution of 2.2 g (9.9 mmol) of lauroyl chloride in 20 mL of dry THF is then added dropwise. The mixture is warmed to room temperature and stirred for 18 hours. The mixture is added to 250 mL of brine and then extracted with 2×200 mL of ether. The combined organic layers are dried over anhydrous magnesium sulfate and concentrated under reduced pressure. The residue is purified by liquid chromatography (LC) (silica gel, ethyl acetate/hexane) to give 3.2 g (74%) of the title compound as a white solid: mp 40°-42° C.

Analysis: Calcd for $C_{29}H_{41}NO_2$: C, 79.9; H, 9.5; N, 3.2. Found: C, 79.9; H, 9.9; N, 3.6.

EXAMPLE 2

1-Hydroxy-2,6-diphenylpiperidin-4-yl Laurate

A solution of 590 mL (27.7 mmol) of dimethyldioxirane, 0.047M in acetone (prepared by the procedure of Eaton and Wicks, J. Org. Chem. 1988, 53, 5353) is added via a cannula to a 0° C. solution of 12.1 g (27.7 mmol) of 2,6-diphenyl-4-piperidyl laurate in 200 mL of acetone. After stirring for 10 minutes at 0° C.; the reaction mixture is concentrated under reduced pressure and the residue is recrystallized from methanol to yield 9.7 g (78% yield) of the title compound as a white solid: mp 89°-90° C.

Analysis: Calcd for $C_{29}H_{41}NO_2$: C, 77.1; H, 9.2; N, 3.1. Found: C, 77.1; H, 9.2; N, 2.9.

EXAMPLE 3

Bis-(2,6-diphenylpiperidin-4-yl) Sebacate

The general procedure of Example 1 is repeated using 2.9 g (11.5 mmol) of 2,6-diphenyl-4-hydroxypiperidine, 4.9 mL (12.0 mmol) of n-butyllithium (2.5M in hexanes) and 1.35 g (5.6 mmol) of sebacoyl chloride. 3.5 g (93% yield) of the title compound is isolated.

EXAMPLE 4

Bis(1-hydroxy-2,6-diphenylpiperidin-4-yl) Sebacate

The general procedure of Example 2 is repeated using 2.0 g (3.0 mmol) of bis-(2,6-diphenylpiperidin-4-yl) sebacate and 82.8 mL (6.0 mmol) of dimethyldioxirane (0.072M in acetone). 1.6 g (76% yield) of the title compound is isolated after recrystallization from methanol: mp 138°-158° C.

Analysis: Calcd for $C_{44}H_{52}N_2O_6$: C, 75.0; H, 7.4; N, 4.0. Found: C, 74.5; H, 7.4; N, 3.8.

EXAMPLE 5

2,6-Diphenyl-3-methylpiperidin-4-yl Laurate

The general procedure of Example 1 is repeated using 22.8 g (85.2 mmol) of 2,6-diphenyl-3-methyl-4-hydroxypiperidine, 34 mL (85 mmol) of n-butyllithium (2.5M in hexanes) and 18.6 g (85.2 mmol) of lauroyl chloride. 25.0 g (65% yield) of the title compound is isolated after purification by LC (silica gel, ethyl acetate/hexane): mp 56°-59° C.

Analysis: Calcd for $C_{30}H_{43}NO_2$: C, 80.1; H, 9.6; N, 3.1. Found: C, 80.8; H, 10.1; N, 3.0.

EXAMPLE 6

1-Hydroxy-2,6-diphenyl-3-methylpiperidin-4-yl Laurate

The general procedure of Example 2 is repeated using 11.5 g (25.5 mmol) of 2,6-diphenyl-3-methylpiperidin-4-yl laurate and 570 mL (25.5 mmol) of dimethyldioxirane (0.045M in acetone). 11.8 g (99% yield) of the title compound is isolated: mp 84°-91° C.

Analysis: Calcd for $C_{30}H_{43}NO_3$: C, 77.4; H, 9.3; N, 3.0. Found: C, 77.0; H, 9.2; N, 2.8.

EXAMPLE 7

2,6-Diphenyl-3,5-dimethylpiperidin-4-yl Laurate

The general procedure of Example 1 is repeated using 28.1 g (0.10 mol) of 2,6-diphenyl-3,5-dimethyl-4-hydroxypiperidine, 40 mL (0.10 mol) of n-butyllithium (2.5M in hexanes) and 21.8 g (0.10 mol) of lauroyl chloride. 34.5 g (74% yield) of the title compound is isolated after purification by LC (silica gel, ethyl acetate/hexane): mp 74°-76° C.

Analysis: Calcd for $C_{31}H_{45}NO_2$: C, 80.3; H, 9.8; N, 3.0. Found: C, 80.0; H, 10.2; N, 2.6.

EXAMPLE 8

1-Hydroxy-2,6-diphenyl-3,5-dimethylpiperidin-4-yl Laurate

The general procedure of Example 2 is repeated using 29.9 g (64.5 mmol) of 2,6-diphenyl-3,5-dimethylpiperidin-4-yl laurate and 1.24 L (64.5 mmol) of dimethyldioxirane (0.050M in acetone). 30.8 g (98% yield) of the title compound is isolated: mp 108°-112° C.

Analysis: Calcd for $C_{31}H_{45}NO_3$: C, 77.6; H, 9.5; N, 2.9. Found: C, 77.5; H, 9.8; N, 2.5.

EXAMPLE 9

Bis-(2,6-diphenyl-3,5-dimethylpiperidin-4-yl) Sebacate

The general procedure of Example 1 is repeated using 18.0 g (64 mmol) of 2,6-diphenyl-3,5-dimethyl-4-hydroxypiperidine, 25.5 mL (64 mmol) of n-butyllithium (2.5M in hexanes) and 7.65 g (32 mmol) of sebacoyl chloride. 2.7 g (12% yield) of the title compound is isolated after purification by LC (silica gel, ethyl acetate/hexane: mp 128°-135° C.

Analysis: Calcd for $C_{48}H_{60}N_2O_4$: C, 79.1; H, 8.3; N, 3.8. Found: C, 78.6; H, 8.2; N, 3.7.

EXAMPLE 10

Bis-(1-hydroxy-2,6-diphenyl-3,5-dimethylpiperidin-4-yl) Sebacate

The general procedure of Example 2 is repeated using 2.09 g (2.86 mmol) of bis-(2,6-diphenyl-3,5-dimethylpiperidin-4-yl) sebacate and 82 mL (5.72 mmol) of dimethyldioxirane (0.070M in acetone). 2.18 g (100% yield) of the title compound is isolated: mp 190°-191° C.

Analysis: Calcd for $C_{48}H_{60}N_2O_6$: C, 75.8; H, 8.0; N, 3.7. Found: C, 75.4; H, 8.0; N, 3.6.

EXAMPLE 11

N-(2,6-Diphenyl-3,5-dimethylpiperidin-4-yl)lauramide

To a stirred 0° C. solution of 12.7 g (45.3 mmol) of 2,6-diphenyl-3,5-dimethyl-4-aminopiperidine and 5.1 g (50 mmol) of triethylamine in 150 ml of methylene chloride is added dropwise a solution of 9.9 g (45.3 mmol) of lauroyl chloride. After stirring for 30 minutes at 0° C., the reaction mixture is washed with water (2×200 ml) followed by a saturated aqueous sodium bicarbonate solution (300 ml). The organic phase is separated, dried over anhydrous magnesium sulfate and then concentrated under reduced pressure. The resulting solid is recrystallized from ethanol to give 15.4 g (73% yield) of the title compound as a white solid melting at 112°-114° C.

Analysis: Calcd for $C_{31}H_{46}N_2O$: C, 80.5; H, 10.0; N, 6.0. Found C, 80.5; H, 10.4; N, 6.0.

EXAMPLE 12

N-(1-Hydroxy-2,6-diphenyl-3,5-dimethylpiperidin-4-yl))lauramide

Following the general procedure of Example 2 and using 8.56 g (18.5 mmol) of N-(2,6-diphenyl-3,5-dimethylpiperidin-4-yl)lauramide, prepared in Example 11, and 462 ml of a 0.04 molar solution of dimethyldioxirane (18.5 mmol) in acetone, the title compound is isolated in a yield of 7.37 g (70%) after purification by LC (silica gel; ethyl acetate:hexanes) as a white solid melting at 58°-62° C.

Analysis: Calcd $C_{31}H_{46}N_2O_2$: C, 77.8; H, 9.7; N, 5.8. Found: C, 77.6; H, 10.2; N, 5.7.

EXAMPLE 13

Process Stabilization of Polypropylene at 525° F. (274° C.)

This example illustrates the process stabilizing effectiveness of the instant compounds in polypropylene.

The base formulation comprises unstabilized, old technology polypropylene (PROFAX 6501, Himont) containing 0.075% by weight of calcium stearate. The test additives are incorporated into the polypropylene by dry blending or, when the additive is a liquid, using a minimum amount of methylene chloride solvent. The solvent is then removed by evaporation under reduced pressure. The stabilized resin formulation is extruded at 90 rpm from a 1 inch (2.54 cm) diameter extruder at 525° F. (274° C.) with a residence time of 90 seconds.

After each of the first and fifth extrusions, the melt flow rate (in grams/10 minutes) is determined by ASTM method D1238 on the pellets obtained from the extruder. The results are given in the table below.

| Additive* | Concentration (% by weight) | Melt Flow after Extrusion | |
| --- | --- | --- | --- |
| | | 1 | 5 |
| None | — | 10.5 | 61.7 |
| Compound of Example 2 | 0.075 | 4.5 | 7.0 |
| Compound of Example 4 | 0.075 | 4.3 | 8.8 |
| Compound of Example 8 | 0.075 | 4.3 | 8.4 |
| Compound of Example 10 | 0.075 | 4.2 | 7.6 |

These results show that the instant 1-hydroxy-2,6-diaryl-4-acyloxypiperidines provide melt flow stabilization to polypropylene as processing stabilizers.

EXAMPLE 14

Process Stabilization of Polypropylene at 525° F. (274° C.)

This example illustrates the process stabilizing effectiveness of the instant compounds in polypropylene in formulations containing a phenolic antioxidant.

The results using the procedure described in Example 13 on polypropylene formulations containing an instant compound and a phenolic antioxidant are given in the table below.

| Additive* | Concentration (% by weight) | Melt Flow after Extrusion 1 | 5 |
|---|---|---|---|
| AO A | 0.075 | 6.7 | 20.2 |
| AO A plus Example 2 | 0.075 0.075 | 3.8 | 6.5 |
| AO A plus Example 4 | 0.075 0.075 | 3.9 | 8.6 |
| AO A plus Example 8 | 0.075 0.075 | 4.3 | 7.4 |
| AO A plus Example 10 | 0.075 0.075 | 4.2 | 8.0 |

*AO A is neopentanetetrayl tetrakis(3,5-di-tert-butyl-4-hydroxyhydrocinnamate).

These results show that the instant 1-hydroxy-2,6-diaryl-4-acyloxypiperidines in combination with a phenolic antioxidant provide melt flow stabilization to polypropylene as processing stabilizers.

EXAMPLE 15

Color Stabilization of Polypropylene

This example illustrates the color stabilizing effectiveness of the instant compounds in combination with a phenolic antioxidant in polypropylene.

Using the procedure described in Example 13, polypropylene containing a phenolic antioxidant in combination with an instant compound is extruded into pellets. Using the pellets obtained after each of the first and fifth extrusions as described in Example 13, the pellets are compression molded into 125 mil (3.2 mm) thick plaques at 193° C. Specimen yellowness index (YI) values are determinated according to ASTM method D1925. Lower YI values indicate less discoloration. The results are given in the table below.

| Additive* | Concentration (% by weight) | Yellowness YI after Extrusion 1 | 5 |
|---|---|---|---|
| AO A | 0.075 | 8.05 | 8.60 |
| AO A plus Example 2 | 0.075 0.075 | 6.45 | 7.40 |
| AO A plus Example 4 | 0.075 0.075 | 6.70 | 7.69 |
| AO A plus Example 8 | 0.075 0.075 | 5.45 | 6.34 |
| AO A plus Example 10 | 0.075 0.075 | 5.91 | 6.48 |

*AO A is neopentanetetrayl tetrakis(3,5-di-tert-butyl-4-hydroxyhydrocinnamate).

These results show that the instant 1-hydroxy-2,6-diaryl-4-acyloxypiperidines in combination with a phenolic antioxidant provide color stabilization to polypropylene as processing stabilizers.

EXAMPLE 16

Long Term Heat Aging Stability of Polypropylene

Extruded pellets (of Example 14), after the first pass, are compression molded into 125 mil (3.2 mm) plaques at 450° F. (232° C.) and then oven aged at 150° C. in a forced draft oven equipped with a rotating carousel. The time, in days, to reach a yellowness index (YI) color of 50 units is deemed to represent failure. The results are given in the table below.

| Additive* | Concentration (% by weight) | Days to Failure |
|---|---|---|
| AO A | 0.075 | 43 |
| AO A plus Example 2 | 0.075 0.075 | 50 |
| AO A plus Example 4 | 0.075 0.075 | 45 |
| AO A plus Example 8 | 0.075 0.075 | 47 |
| AO A plus Example 10 | 0.075 0.075 | 38 |

*AO A is neopentanetetrayl tetrakis(3,5-di-tert-butyl-4-hydroxyhydrocinnamate).

EXAMPLE 17

Long Term Heat Aging Stability of Polypropylene

Extruded pellets (of Example 14), after the first pass, are compression molded into 40 mil (1 mm) plaques at 450° F. (232° C.) and then oven aged at 150° C. in a forced draft oven equipped with a rotating carousel. The time, in days, to physical failure is determined by a 90° bend test. The results are given in the table below.

| Additive* | Concentration (% by weight) | Days to Failure |
|---|---|---|
| AO A | 0.075 | 28 |
| AO A plus Example 2 | 0.075 0.075 | 31 |
| AO A plus Example 4 | 0.075 0.075 | 38 |
| AO A plus Example 8 | 0.075 0.075 | 38 |
| AO A plus Example 10 | 0.075 0.075 | 34 |

*AO A is neopentanetetrayl tetrakis(3,5-di-tert-butyl-4-hydroxyhydrocinnamate).

EXAMPLE 18

Oxidative Induction Time

Extruded pellets (of Example 14), after the first pass, are analyzed by DSC using aluminum pans/isothermal at 190° C. under oxygen according to ASTM-3895-80. The time of onset and peak are is given in minutes. The results are given in the table below.

| Additive* | Concentration (% by weight) | OIT Onset Minutes | OIT Peak Minutes |
|---|---|---|---|
| AO A | 0.075 | 16 | 21 |
| AO A plus Example 2 | 0.075 0.075 | 42 | 50 |
| AO A plus Example 4 | 0.075 0.075 | 31 | 28 |
| AO A plus Example 8 | 0.075 0.075 | 30 | 38 |
| AO A plus Example 10 | 0.075 0.075 | 28 | 37 |

*AO A is neopentanetetrayl tetrakis(3,5-di-tert-butyl-4-hydroxyhydrocinnamate).

What is claimed is:

1. A compound which is a substituted 2,6-diaryl-4-acyloxypiperidine or 2,6-diaryl4-acylaminopiperidine of formula II

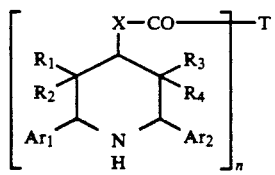

(II)

wherein
n is 1, 2, 3 or 4;
X is —O— or —NE—,
E is hydrogen, alkyl of 1 to 20 carbon atoms or cycloalkyl of 5 to 12 carbon atoms,
$Ar_1$ and $Ar_2$ are independently carbocyclic aryl of 6 to 10 carbon atoms; or said aryl substituted by one to three substituents selected from the group consisting of alkyl of 1 to 20 carbon atoms; cycloalkyl of 5 to 12 carbon atoms; phenylalkyl of 7 to 15 carbon atoms; —$COOR_5$ where $R_5$ is hydrogen or alkyl of 1 to 20 carbons; —$COR_6$ where $R_6$ is alkyl of 1 to 20 carbons; —$NR_7R_8$ where $R_7$ and $R_8$ are independently hydrogen or alkyl of 1 to 20 carbons; —$SR_9$ where $R_9$ is carbocyclic aryl of 6 to 10 carbon atoms or alkyl of 1 to 20 carbon atoms; —OH; —$OCH_3$; —CN; —$CF_3$; —$NO_2$; —F; —Cl; —Br and —I;
$R_1$, $R_2$, $R_3$ and $R_4$ are independently hydrogen; a linear or branched alkyl of 1 to 30 carbon atoms; or said alkyl terminated with —$OR_{10}$, —$NR_{11}R_{12}$, —$SR_{13}$, —$COOR_{14}$ or —$CONR_{15}R_{16}$, where $R_{10}$, $R_{11}$, $R_{12}$, $R_{13}$ and $R_{14}$ are independently alkyl of 1 to 20 carbon atoms or alkenyl of 3 to 18 carbon atoms, and $R_{15}$ and $R_{16}$ are independently hydrogen or the same meaning as $R_{10}$; or said alkyl interrupted by one or two —O—, —S—, —SO—, —$SO_2$—, —CO—, —COO—, —OCO—, —$CONR_{17}$—, —$NR_{17}CO$— or —$NR_{18}$— where $R_{17}$ and $R_{18}$ have the same meaning as $R_{15}$; alkenyl of 3 to 20 carbon atoms; carbocyclic aryl of 6 to 10 carbon atoms; or said aryl substituted by one to three substituents selected from the group consisting of alkyl of 1 to 20 carbon atoms, cycloalkyl of 5 to 12 carbon atoms, and phenylalkyl of 7 to 15 carbon atoms; and when n is 1, T is alkyl of 1 to 20 carbon atoms or said alkyl interrupted by one or two of —O—, —S—, —SO—, —$SO_2$—, —CO—, —COO—, —OCO—, —$CONR_{19}$—, —$NR_{19}CO$— or —$NR_{20}$— where $R_{19}$ and $R_{20}$ have the same meaning as $R_{15}$; or carbocyclic aryl or substituted aryl having the same definition as $Ar_1$;

when n is 2, T is a direct bond; alkylene of 1 to 12 carbon atoms, or said alkylene interrupted by one or two of —O—, —S—, —SO—, —$SO_2$—, —CO—, —COO—, —OCO—, —$CONR_{21}$, —$NR_{21}CO$— or —$NR_{22}$— where $R_{21}$ and $R_{22}$ have the same meaning as $R_{15}$;

when n is 3, T is alkanetriyl of 3 to 8 carbon atoms; and when n is 4, T is alkanetetrayl of 4 to 10 carbon atoms.

2. A compound according to claim 1 wherein n is 1 or 2.

3. A compound according to claim 1 wherein $Ar_1$ and $Ar_2$ are the same and each is phenyl or phenyl substituted by methyl.

4. A compound according to claim 3 wherein $Ar_1$ and $Ar_2$ are phenyl.

5. A compound according to claim 1 wherein $R_1$, $R_2$, $R_3$ and $R_4$ are independently hydrogen or methyl.

6. A compound according to claim 5 wherein each of $R_1$, $R_2$, $R_3$ and $R_4$ is hydrogen; or $R_1$ is methyl, and $R_2$, $R_3$ and $R_4$ are hydrogen; or $R_1$ and $R_3$ are methyl, and $R_2$ and $R_4$ are hydrogen.

7. A compound according to claim 1 wherein, when n is 1, T is alkyl of 1 to 17 carbon atoms.

8. A compound according to claim 7 wherein, when n is 1, T is alkyl of 7 to 17 carbon atoms.

9. A compound according to claim 1 wherein, when n is 2, T is alkylene of 2 to 10 carbon atoms.

10. A compound according to claim 9 wherein, when n is 2, T is alkylene of 2 to 8 carbon atoms.

11. A compound according to claim 1 wherein X is —O—.

12. The compound according to claim 1 which is
2,6-diphenylpiperidin-4-yl laurate;
bis(2,6-diphenylpiperidin-4-yl) sebacate;
2,6-diphenyl-3-methylpiperidin-4-yl laurate;
2,6-diphenyl-3,5-dimethylpiperidin-4-yl laurate;
bis(2,6-diphenyl-3,5-dimethylpiperidin-4-yl) sebacate; or
N-(2,6-diphenyl-3,5-dimethylpiperidin-4-yl)lauramide.

* * * * *